US012728145B2

(12) United States Patent
Chen et al.

(10) Patent No.: US 12,728,145 B2
(45) Date of Patent: Sep. 8, 2026

(54) MANGOSTEEN PERICARP EXTRACTAND PROCESS FOR ITS PREPARATION THEREOF

(71) Applicant: JUNHONG BIOTECHNOLOGY CO., LTD., Taipei (TW)

(72) Inventors: Chia-Wen Chen, Taipei (TW); Rong-Hong Hsieh, Taipei (TW); Yen-Ting Chen, Taipei (TW); Yin-Jun Chen, Taipei (TW); Hsin Yuan, Taipei (TW); Chih-Hsin Huang, Taipei (TW)

(73) Assignee: JUNHONG BIOTECHNOLOGY CO., LTD., Taipei City (TW)

( * ) Notice: Subject to any disclaimer, the term of this patent is extended or adjusted under 35 U.S.C. 154(b) by 377 days.

(21) Appl. No.: 18/074,255

(22) Filed: Dec. 2, 2022

(65) Prior Publication Data

US 2023/0149491 A1 May 18, 2023

Related U.S. Application Data

(63) Continuation-in-part of application No. 17/380,408, filed on Jul. 20, 2021, now Pat. No. 11,517,601.

(30) Foreign Application Priority Data

Jul. 21, 2020 (TW) ................................ 109124499

(51) Int. Cl.

| | |
|---|---|
| ***A61K 36/38*** | (2006.01) |
| ***A23K 10/30*** | (2016.01) |
| ***A23L 33/00*** | (2016.01) |
| ***A23L 33/105*** | (2016.01) |
| ***A61K 31/352*** | (2006.01) |
| ***B01D 11/02*** | (2006.01) |

(52) U.S. Cl.

CPC .............. *A61K 36/38* (2013.01); *A23K 10/30* (2016.05); *A23L 33/105* (2016.08); *A23L 33/40* (2016.08); *A61K 31/352* (2013.01); *B01D 11/0288* (2013.01); *A23V 2002/00* (2013.01); *A61K 2236/17* (2013.01); *A61K 2236/33* (2013.01); *A61K 2236/53* (2013.01)

(58) Field of Classification Search

None

See application file for complete search history.

(56) References Cited

U.S. PATENT DOCUMENTS

| | | | |
|---|---|---|---|
| 7,285,672 | B2 | 10/2007 | Sobotta et al. |
| 10,471,114 | B2 | 11/2019 | Gokaraju et al. |
| 2006/0088643 | A1 | 4/2006 | Fugal et al. |

FOREIGN PATENT DOCUMENTS

| | | | |
|---|---|---|---|
| CN | 102241659 | A | 11/2011 |
| CN | 101525328 | B | 8/2012 |
| CN | 103467433 | A | 12/2013 |
| JP | WO2006137139 | A1 | 1/2009 |
| TW | I627960 | B | 7/2018 |
| WO | WO2006/137139 | A1 | 12/2006 |

OTHER PUBLICATIONS

Thomas EL, Frost G, Taylor-Robinson SD, Bell JD. Excess body fat in obese and normal-weight subjects. Nutr Res Rev. Jun. 2012;25(1):150-61.

Fukuda T, Bouchi R, Takeuchi T, Nakano Y, Murakami M, Minami I, Izumiyama H, Hashimoto K, Yoshimoto T, Ogawa Y. Ratio of visceral-to-subcutaneous fat area predicts cardiovascular events in patients with type 2 diabetes. J Diabetes Investig. Mar. 2018;9(2):396-402.

Miao Z, Alvarez M, Ko A, Bhagat Y, Rahmani E, Jew B, Heinonen S, Muñoz-Hernandez LL, Herrera-Hernandez M, Aguilar-Salinas C, Tusie-Luna T, Mohlke KL, Laakso M, Pietiläinen KH, Halperin E, Pajukanta P. The causal effect of obesity on prediabetes and insulin resistance reveals the important role of adipose tissue in insulin resistance. PLoS Genet. Sep. 14, 2020;16(9):e1009018.

Wali JA, Jarzebska N, Raubenheimer D, Simpson SJ, Rodionov RN, O'Sullivan JF. Cardio-Metabolic Effects of High-Fat Diets and Their Underlying Mechanisms—A Narrative Review. Nutrients. May 21, 2020;12(5):1505.

Lee YS, Li P, Huh JY, Hwang IJ, Lu M, Kim JI, et al. Inflammation is necessary for long-term but not short-term high-fat diet-induced insulin resistance. Diabetes. 2011; 60:2474-2483.

Roel A van der Heijden, Fareeba Sheedfar, Martine C Morrison, Pascal PH Hommelberg, Danny Kor, Niels J Kloosterhuis, Nanda Gruben, Sameh A Youssef, Alain de Bruin, Marten H Hofker, Robert Kleemann, Debby PY Koonen, Peter Heeringa. High-fat diet induced obesity primes inflammation in adipose tissue prior to liver in C57BL/6j mice. Aging (Albany NY) Apr. 2015; 7(4): 256-267.

Chen LG, Yang LL, Wang CC. Anti-inflammatory activity of mangostins from Garcinia mangostana. Food Chem Toxicol. 2008; 46:688-693.

Chairungsrilerd N, Furukawa K, Ohta T, Nozoe S, Ohizumi Y. Histaminergic and serotonergic receptor blocking substances from the medicinal plant *Garcinia mangostana*. Planta Med. Oct. 1996;62(5):471-2.

(Continued)

*Primary Examiner* — Michael V Meller

(74) *Attorney, Agent, or Firm* — MUNCY, GEISSLER, OLDS & LOWE, P.C.

(57) ABSTRACT

The present invention discloses a mangosteen pericarp extract and process for its preparation thereof. The mangosteen pericarp extract containing α-mangostin and γ-mangostin which obtains from preparation steps comprising fragmentation, organic solvent soaking, aqueous solution, or acidic solution soaking, concentration, spray drying and grinding steps from the rind of the mangosteen. The present invention has advantages of simple preparation process to address efficiency issue, no need to have heating under reflux in extraction steps and the solvents which used are friendly to human body and environment. The mangosteen pericarp extract (α-Xones Prime) can significantly decrease insulin resistance, and bodyweight gain induced by daily high fat diet intake. In addition, administration of the mangosteen pericarp ethanolic extract can reduce fat accumulation in the adipose and muscle tissue of rats with daily high fat diet intake. The α-Xones Prime could be used as a nutraceutical ingredient for weight control or weight loss, or even prevention of metabolic syndrome and diabetes, and developed into a candidate drug composition.

1 Claim, 4 Drawing Sheets
(2 of 4 Drawing Sheet(s) Filed in Color)

(56) References Cited

OTHER PUBLICATIONS

Li D, Liu Q, Lu X, Li Z, Wang C, Leung CH, Wang Y, Peng C, Lin L. α-Mangostin remodels visceral adipose tissue inflammation to ameliorate age-related metabolic disorders in mice. Aging (Albany NY) 2019; 11:11084-11110.

Jiang HZ, Quan XF, Tian WX, Hu JM, Wang PC, Huang SZ, Cheng ZQ, Liang WJ, Zhou J, Ma XF, Zhao YX. Fatty acid synthase inhibitors of phenolic constituents isolated from Garcinia mangostana. Bioorg Med Chem Lett. Oct. 15, 2010;20(20):6045-7.

MANGOSTEEN PERICARP EXTRACTAND PROCESS FOR ITS PREPARATION THEREOF

CROSS-REFERENCE TO RELATED APPLICATIONS

This application is a continuation-in-part of U.S. patent application Ser. No. 17/380,408, filed on Jul. 20, 2021, which claims the priority benefits of Taiwan Patent Application No. 109124499, filed on Jul. 21, 2020. The entirety the above-mentioned patent application is hereby incorporated by reference herein and made a part of this specification.

FIELD OF THE INVENTION

The present invention is related to the technical field of mangosteen pericarp extract and process for its preparation thereof, particularly a mangosteen pericarp extract containing α-mangostin and γ-mangostin and a process for preparing the mangosteen pericarp extract.

The present invention relates to application of the mangosteen pericarp ethanolic extract (α-Xones Prime) to inhibits weight gain, insulin resistance, and fat accumulation in adipose and muscle tissue induced by daily intake of high fat diet.

BACKGROUND OF THE INVENTION

Some studies have shown that the rind of the mangosteen has special phytochemicals which is "Xanthone". The xanthone had be found that it has a distinct chemical structure, known as tricyclic aromatic system, which consist of two benzene rings attached through a carbonyl group (C6-C1-C6 structure) and oxygen. It has various of chemical names due to the binding of different functional groups such as hydroxyl group and isoprene. α-mangostin and γ-mangostin are two members of the class of xanthone in mangosteen pericarp which have higher proportion, and they exhibited antibacterial effect, as well as antioxidant effect caused by great chelating activity. Recent researches found that mangostin can protect pancreatic cells and lower blood sugar levels in diabetic subjects and therefore the mangosteen pericarp extracts are often used to be prepared functional food and supplements.

Currently, microwave extraction method and Soxhlet extraction method are two common methods be used for extracting xanthone from the rind of the mangosteen, and the methods need to heat organic solvent including ethyl acetate, methanol, ethanol, petroleum ether, and other aromatic compounds under reflux process due to xanthone is water-insoluble substance and to implement freeze drying or spray drying process to obtain the crude extracted product. In order to obtain higher purity extracted product, need to undergo fractional distillation or use another organic solvent including dichloromethane, petroleum ether or toluene to conduct secondary extraction. For example, U.S. Pat. No. 7,285,672 describes a process for isolating and purifying pure α-mangostin from the rind of mangosteen fruit, its step comprising: the plant material is pre-softened in water for 12-13 hours and is combined with three times the amount of toluene as extracting solvent to extract the plant material at 59 to 70° C., and then is conducting concentration and recrystallisation processes; dissolving the crude product in a mixture of 1,2-ethanediol and toluene in a ratio of about 96:4 at 80° C.; cooling to room temperature and filtering the solution; recrystallization process is carried out with ethanol/water to obtain α-mangostin. China patent NO. 103467433 discloses a method for extracting α-mangostin and the method comprising the mangosteen pericarp is pulverized and is combined with eight to ten times the amount of aqueous solution to perform one to two times reflux extraction and one to three hours for each time; using eight to ten times the amount of 90% to 95% ethanol solution to perform one to three times reflux extraction and one to three hours for each time; concentrating, isolating and drying to obtain crude product; using weight ratio 60:70 to 30:40 of dimethyl ether and butane as extracting solvent to perform subcritical fluid extraction and then to obtain high purity of α-mangostin after solvent is evaporated. China patent No. 101525328 also discloses a method using chloroform and ethyl acetate as organic solvent to obtain high purity of α-mangostin. International application No. PCT/JP2005/011502 (published as WO/2006/137139) provides a method of isolating a mangosteen derivative and the steps comprising to heat and wash mangosteen pericarp by adding water at 90° C.; to perform extraction and filtration process at 50 to 85° C. after adding concentration of 25~75% ethanol to obtain crude product; dissolving crude product with ethanol with a concentration of 25~75%; obtaining purified mangosteen derivative after recrystallization, and the purified mangosteen derivative has total amount of 90% α-mangostin and γ-mangostin and the content ratio of α-mangostin to γ-mangostin is 75~85% to 7~75%.

Conventional extraction techniques arise several problems. First, the steps are complicated and must consume energy for heating and refluxing. Second, most of methods only can generate single kind of xanthone, usually α-mangostin, and different kind and content of xanthone can not be obtained from a single preparation process. Third, need to use organic solvents with high toxicity such as dichloromethane, petroleum ether or toluene which are harmful to human body and the environment.

The incidence of obesity has become a major public health concern worldwide. Obesity is characterized by the accumulation and deposition of excess fat in adipose tissues [1] and increased deposition of cytoplasmic triglycerides [2]. Adipose tissue is an important site of inflammatory events in obesity. It contains various cell types that all contribute to the inflammatory response during obesity. In addition to regulating fat mass and nutrient homeostasis, adipocytes mediate the inflammatory response through the secretion of adipokines, cytokines, and chemokines, which may lead to various metabolic and chronic diseases such as cardiovascular diseases, type 2 diabetes, and cancer [3, 4]. Previous studies have found that insulin resistance (IR) may be related to obesity and skeletal mitochondrial dysfunction. Skeletal muscle accounts for approximately 80% of insulin-stimulated glucose uptake, and one of the key causes of diabetes mellitus type 2 (T2DM) is insulin resistance in skeletal muscle [5]. Furthermore, high-fat diet (HFD) feeding is associated with adipose tissue inflammation and importance to the development of metabolic inflammation and IR in diet-induced obesity in mice. [6]. Therefore, it is very important to reduce metabolic inflammation or prevent obesity. Chen et al. (7) and Chairungsrilerd et al. (8) found that α-mangostin and γ-mangostin from *G. mangostana* have been proven to possess anti-inflammatory properties, respectively in several in vitro and in vivo models.

In addition, Li et al (9) found that the anti-obesity and hepatoprotective effects of α-mangostin are mediated via the sirtuin 1 (SIRT1)-AMP-activated protein kinase (AMPK) and peroxisome proliferator-activated receptor γ (PPARγ)

pathways in mice with obesity induced by a high fat diet. Jiang et al. (10) isolated a series of xanthones (including α-mangostin, γ-mangostin and garcinone E), and assayed for their inhibitory activities against fatty acid synthase (FAS). Overall, xanthones from *G. mangostana* showed great anti-adipogenic activity, through suppressing PPARγ expression and FAS activity. Although the anti-adipogenic activity of xanthones from *G. mangostana* has been widely investigated, no in vivo study has verified that these xanthones are able to prevent or treat obesity directly. Therefore, an object of the invention is to provide the mangosteen pericarp ethanolic extract (α-Xones Prime) has inhibitory effects on weight gain, insulin resistance, and fat accumulation in adipose and muscle tissues of the obesity animal model induced by daily intake of high fat diet.

Some of the patents are quoted below which refer to the treatment and curing of obesity and other metabolic disorders.

PCT Publication U.S. Pat. No. 10,471,114B2 discloses pharmaceutical/dietary supplements and food ingredient(s) derived from *Sphaeranthus indicus* and *Garcinia mangostana* extract(s), fraction(s), active compound(s) and phytochemical(s) or mixtures thereof and their compositions. The ingredients and the composition(s) can be used for the control, prevention and treatment of obesity, metabolic syndrome, diabetes and other metabolic disorders, and also to regulate energy expenditure, prevention of atherosclerotic plaques in coronary artery and abdominal aorta, increase insulin sensitivity, improve glucose tolerance, lower triglyceride levels and balance glucose levels in mammals.

PCT Publication US20060088643A1 discloses A nutraceutical beverage comprising pericarp extract from the *Garcinia mangostana* L. (mangosteen) plant, and juice from mangosteen fruit pulp, preferably combined with juice from at least one of four other ingredients selected from red grapes, *lycium*, sea buckthorn, and apple, preferably obtained from powdered extract of mangosteen pericarp and a mixture of fruit concentrate and/or powdered fruit and/or fruit extract. The nutraceutical beverage is beneficial for antioxidants in the body and stimulating a cellular immune system response.

REFERENCES (1) Thomas E L, Frost G, Taylor-Robinson S D, Bell J D. Excess body fat in obese and normal-weight subjects. Nutr Res Rev. 2012 June; 25 (1): 150-61.

(2) Fukuda T, Bouchi R, Takeuchi T, Nakano Y, Murakami M, Minami I, Izumiyama H, Hashimoto K, Yoshimoto T, Ogawa Y. Ratio of visceral-to-subcutaneous fat area predicts cardiovascular events in patients with type 2 diabetes. J Diabetes Investig. 2018 March; 9 (2): 396-402.

(3) Miao Z, Alvarez M, Ko A, Bhagat Y, Rahmani E, Jew B, Heinonen S, Muñoz-Hernandez L L, Herrera-Hernandez M, Aguilar-Salinas C, Tusie-Luna T, Mohlke K L, Laakso M, Pietiläinen K H, Halperin E, Pajukanta P. The causal effect of obesity on prediabetes and insulin resistance reveals the important role of adipose tissue in insulin resistance. PLOS Genet. 2020 Sep. 14; 16 (9): e1009018.

(4) Wali J A, Jarzebska N, Raubenheimer D, Simpson S J, Rodionov R N, O'Sullivan J F. Cardio-Metabolic Effects of High-Fat Diets and Their Underlying Mechanisms-A Narrative Review. Nutrients. 2020 May 21; 12 (5): 1505.

(5) Lee Y S, Li P, Huh J Y, Hwang I J, Lu M, Kim J I, et al. Inflammation is necessary for long-term but not short-term high-fat diet-induced insulin resistance. Diabetes. 2011; 60:2474-2483.

(6) Roel A van der Heijden, Fareeba Sheedfar, Martine C Morrison, Pascal P H Hommelberg, Danny Kor, Niels J Kloosterhuis, Nanda Gruben, Sameh A Youssef, Alain de Bruin, Marten H Hofker, Robert Kleemann, Debby P Y Koonen, Peter Heeringa. High-fat diet induced obesity primes inflammation in adipose tissue prior to liver in C57BL/6j mice. Aging (Albany NY) 2015 April; 7 (4): 256-267.

(7) Chen L G, Yang L L, Wang C C. Anti-inflammatory activity of mangostins from *Garcinia mangostana*. Food Chem Toxicol. 2008; 46:688-693.

(8) Chairungsrilerd N, Furukawa K, Ohta T, Nozoe S, Ohizumi Y. Histaminergic and serotonergic receptor blocking substances from the medicinal plant *Garcinia mangostana*. Planta Med. 1996 October; 62 (5): 471-2.

(9) Li D, Liu Q, Lu X, Li Z, Wang C, Leung C H, Wang Y, Peng C, Lin L. α-Mangostin remodels visceral adipose tissue inflammation to ameliorate age-related metabolic disorders in mice. Aging (Albany NY) 2019; 11:11084-11110.

(10) Jiang H Z, Quan X F, Tian W X, Hu J M, Wang P C, Huang S Z, Cheng Z Q, Liang W J, Zhou J, Ma X F, Zhao Y X. Fatty acid synthase inhibitors of phenolic constituents isolated from *Garcinia mangostana*. Bioorg Med Chem Lett. 2010 Oct. 15; 20 (20): 6045-7.

SUMMARY OF THE INVENTION

In view of the above problems, the present invention is directed to a mangosteen pericarp extract and process for its preparation with simple preparation steps to address efficiency issue and with advantage of having α-mangostin and γ-mangostin in the extract product from the rind of the mangosteen in the same preparation process.

To achieve the objectives, a preparation process for mangosteen pericarp extract of the present invention comprising:

drying and fragmenting the mangosteen pericarp to obtain fragment of mangosteen pericarp;

soaking the fragment of mangosteen pericarp in organic solvent with a concentration of at least 70% and placing it at room temperature, and filtering it to obtain a mangosteen pericarp organic solvent extract, wherein the ratio of the weight to volume of the fragment of mangosteen pericarp and the organic solvent is 1:5 to 1:20;

soaking and heating the fragment of mangosteen pericarp obtained from the previous step in aqueous solution and placing it at room temperature, and filtering it to obtain a mangosteen pericarp aqueous extract and a mangosteen pericarp residue, wherein the ratio of the weight to volume of the fragment of mangosteen pericarp and the aqueous solution is 1:10 to 1:20;

concentrating the mangosteen pericarp organic solvent extract and the mangosteen pericarp aqueous extract to obtain a mangosteen pericarp organic solvent concentrate and a mangosteen pericarp aqueous concentrate; and spray drying the mangosteen pericarp organic solvent concentrate to obtain a α-Xones Extract, wherein the α-Xones Extract containing 10% to 30% of xanthone.

The process mentioned above further comprising the following steps:

adding a first specific amount of the aqueous or acidic solution into the mangosteen pericarp organic solvent concentrate, homogenizing it, placing it at room temperature, and separating it into a first upper layer aqueous solution and a first lower layer precipitate;

isolating the first upper layer aqueous solution and adding a second specific amount of ethanol to dissolve the first lower layer precipitate, and obtaining a mangosteen pericarp ethanol filtrate by filtration; and spray drying the mangosteen pericarp aqueous concentrate and the first upper layer aqueous solution to obtain α-Xones Aqua Choice.

The process mentioned above further comprising the following steps:

adding alkane solvent with volume ratio is 1:1 to 1:10 into the mangosteen pericarp ethanol filtrate and mixing by vortex mixer, placing it at room temperature, and separating it into an upper layer alkane solvent and a lower layer ethanol filtrate;

heating and concentrating the lower layer ethanol filtrate in water bath to obtaining a lower layer ethanol concentrated filtrate, and adding and mixing aqueous solution with volume ratio is 1:1 to 3:1 into the lower layer ethanol concentrated filtrate, placing it at low temperature, and separating it into a second upper layer aqueous solution and a second lower layer precipitate; and fragmenting, air-lay drying and grinding the second lower layer precipitate to obtain α-Xones Prime, wherein the α-Xones Prime containing at least 50% of xanthone.

The process mentioned above further comprising the following steps:

air-lay drying and grinding the mangosteen pericarp residue to obtain α-Xones Prebio.

The organic solvent in the process mentioned above is methanol, ethanol, ethyl acetate or chloroform.

The aqueous solution in the process mentioned above is distilled water, deionized water or solutions prepared from acid salts or metal ion salts. The acidic solution is formic acid, propionic acid, hydrochloric acid, phosphoric acid, sulfuric acid, carbonic acid, acetic acid, citric acid, or oxalic acid. The α-Xones Aqua Choice containing 1% to 5% of mangosteen water-soluble polyphenol, and the mangosteen water-soluble polyphenol comprising chlorogenic acid, epicatechin and procyanidins.

The alkane solvent in the process mentioned above is in liquid form at room temperature.

To achieve the objectives, a mangosteen pericarp extract of the present invention comprising at least 10% of xanthone, wherein the xanthone containing 65% to 75% of α-mangostin and 10% to 15% of γ-mangostin.

The mangosteen pericarp extract mentioned above comprising at least 30% of xanthone.

The mangosteen pericarp extract mentioned above comprising at least 50% of xanthone.

Mangosteen pericarp ethanolic extract inhibits weight gain, insulin resistance, and fat accumulation in adipose and muscle tissue induced by a high-fat diet The present invention discloses the mangosteen pericarp ethanolic extract (α-Xones Prime) by the patented process can significantly decrease insulin resistance, and body-weight gain induced by daily high fat diet intake. In addition, administration of the mangosteen pericarp ethanolic extract can reduce fat accumulation in the adipose and muscle tissue of rats with daily high fat diet intake. The α-Xones Prime could be used as a nutraceutical ingredient for weight control or weight loss, or even prevention of metabolic syndrome and diabetes, and developed into a candidate drug composition.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENTS

Figure 1A:
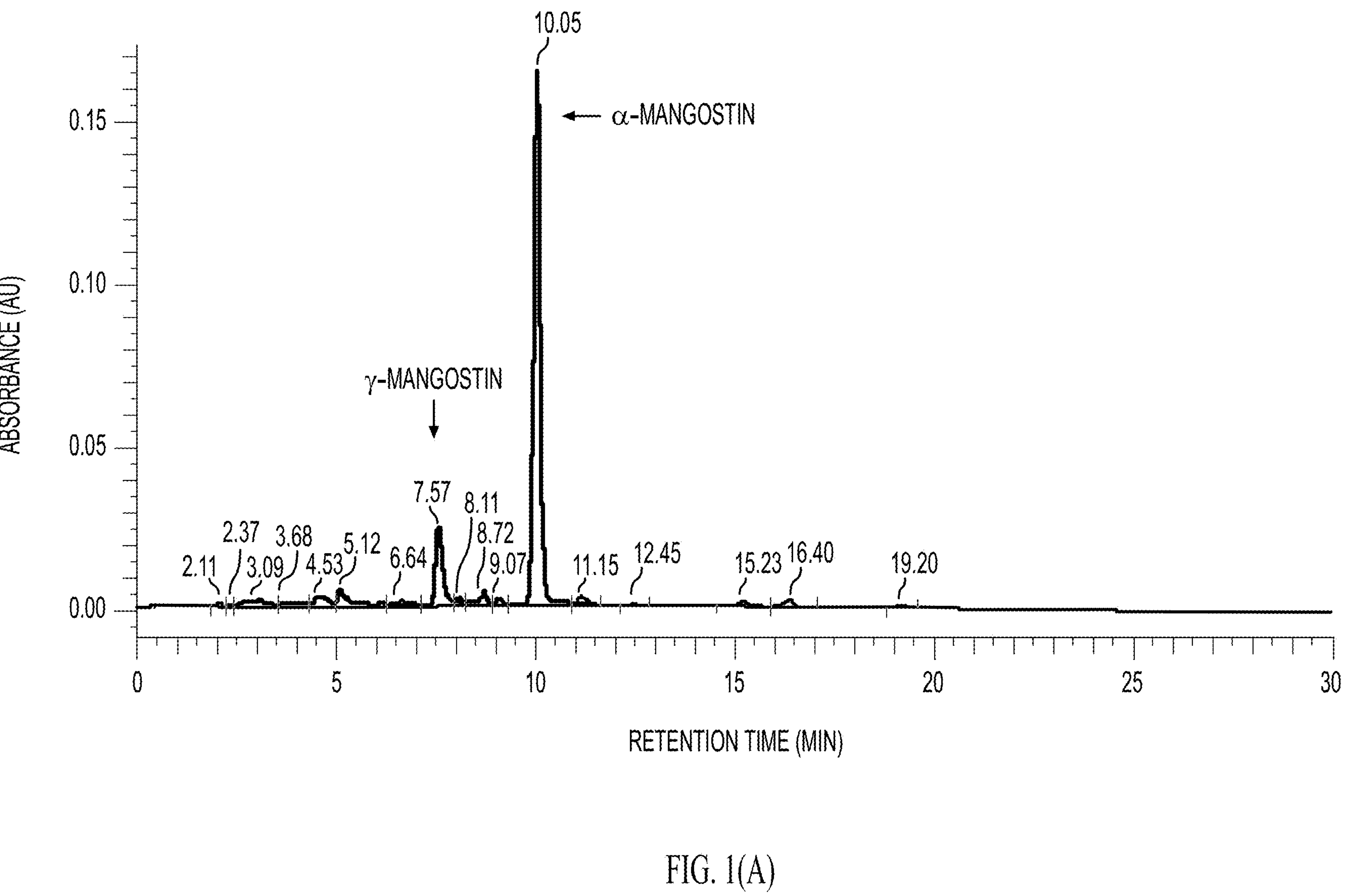
FIG. 1(A) is an analysis result of ratio of α-mangostin and γ-mangostin in the extract of the present invention.

In order to fully comprehend the objectives, features and efficacy of the present invention, a detailed description is described by the following substantial embodiments in conjunction with the accompanying drawings. The description is as below.

As used herein, the description of unit, element and component in the present invention uses "one", "a", or "an". The way mentioned above is for convenience, and for general meaning of the category of the present invention. Therefore, the description should be understood as "include one", "at least one", and include the singular and plural forms at the same time unless obvious meaning.

As used herein, the description of "comprising", "comprises", "include", "includes", "including" and other similar terms used in the present invention are meant to be non-limiting. For example, it may include any components or ingredients that are not specifically listed in the description.

The mangosteen pericarp extract preparation process of the present invention is first drying and fragmenting the mangosteen pericarp to obtain fragment of mangosteen pericarp. To facilitate subsequent extraction operations, the fragment could be divided and packaged by food grade of cotton filter bags or stainless-steel filter buckets. The fragment of mangosteen pericarp is soaked in organic solvent with certain concentration and ratio and is placed at room temperature for a while, and then to perform filtering to obtain a mangosteen pericarp organic solvent extract, wherein the certain ratio means the weight to volume of the fragment of mangosteen pericarp and the organic solvent is 1:5 to 1:20, preferably 1:5 to 1:10, and the certain concentration means volume percentage concentration is at least 70%, preferably at least 80%, more preferably at least 90%, the organic solvent including but not limit to methanol, ethanol, acetic acid, ethyl acetate and chloroform. Following soaked in organic solvent, the fragment of mangosteen pericarp is soaked in aqueous solution with certain ratio and is placed at room temperature after heating, and then is filtered to obtain a mangosteen pericarp aqueous extract and a mangosteen pericarp residue, wherein the ratio means the weight to volume of the fragment of mangosteen pericarp and the aqueous solution is 1:10 to 1:20, preferably 1:10 to 1:20. α-Xones Prebio can be obtained by spray drying at 40 to 60° C. and grinding the mangosteen pericarp residue, especially, α-Xones Prebio in the present invention refers to a mangosteen pericarp extract of its fiber. To concentrate the mangosteen pericarp organic solvent extract and the mangosteen pericarp aqueous extract to obtain a mangosteen pericarp organic solvent concentrate and a mangosteen pericarp aqueous concentrate and α-Xones Extract can be obtained by spray drying of the mangosteen pericarp organic solvent concentrate, especially, α-Xones Extract in the present invention refers to a low purity of the mangosteen pericarp extract containing 10% to 30% of xanthone.

Following the process mentioned above, the process further comprising the steps of adding amount of the aqueous or acidic solution into the mangosteen pericarp organic solvent concentrate and homogenizing, and be separated into a first upper layer aqueous solution and a first lower layer precipitate after being placed at room temperature for a while, then isolating the first upper layer aqueous solution and adding amount of ethanol to dissolve the first lower layer precipitate and be filtered to obtain a mangosteen pericarp ethanol filtrate; and α-Xones Aqua Choice can be obtained by spray drying the mangosteen pericarp aqueous solution concentrate and the first upper layer aqueous solution, wherein the weight to volume of first lower layer precipitate and ethanol is 1:1 to 1:2, preferably 1:1 to 1:1.5, especially, α-Xones Aqua Choice in the present invention refers to mangosteen pericarp water-soluble extract containing 1 to 5% of mangosteen water-soluble polyphenol including but not limit to polyphenol comprising chlorogenic acid, epicatechin and procyanidins.

Following the process mentioned above, the process further comprising the steps of adding alkane solvent with volume ratio is 1:1 to 1:10 into the mangosteen pericarp ethanol filtrate and mixing it to as suspension by vortex mixer and be separated into an upper layer alkane solvent and a lower layer ethanol filtrate after being placed at room temperature for a while, wherein the alkane solvent refers to alkanes in liquid form at room temperature, which including but not limit to N-pentane, N-hexane, and N-heptane. Next, the lower layer ethanol filtrate is isolated and heated in water bath and is concentrated at low temperature to obtain a lower layer ethanol concentrated filtrate and then to add and mix aqueous solution with volume ratio is 1:1 to 3:1 into the lower layer ethanol concentrated filtrate, and it would be separated into a second upper layer aqueous solution and a second lower layer precipitate after being placed at low temperature for a while. Then, α-Xones Prime can be obtained by fragmenting, spray drying, and grinding the second lower layer precipitate, especially, the α-Xones Prime in the present invention refers to a high purity of the mangosteen pericarp extract containing at least 50% of xanthone.

Example 1

To obtain fragment of mangosteen pericarp by drying and fragmenting the mangosteen pericarp and then the fragment is divided and packaged to a food grade of stainless-steel filter bucket. The fragment of mangosteen pericarp is soaked in ethyl acetate with the ratio of weight to volume of 1:5 and the concentration of 70% and is placed at room temperature overnight and then to perform filtering to obtain a mangosteen pericarp ethyl acetate extract. Next, the fragment of mangosteen pericarp is soaked in distilled water with ratio of weight to volume of 1:10 and is placed at room temperature overnight after heating at 95° C. for two hours; mangosteen pericarp water extract and mangosteen pericarp residue both be isolated by filter, and then α-Xones Prebio can be generated by spray drying and grinding the mangosteen pericarp residue at 40 to 60° C. Next, to concentrate the mangosteen pericarp ethyl acetate extract and the mangosteen pericarp water extract to obtain a mangosteen pericarp ethyl acetate concentrate and a mangosteen pericarp water concentrate, and then spray drying the mangosteen pericarp ethyl acetate concentrate to obtain α-Xones Extract, wherein the α-Xones Extract containing about 10% of xanthone (based on the total content of α-mangostin and γ-mangostin) and the percent yield is 40% to the initial weight of mangosteen pericarp. Moreover, to add amount of distilled water into the mangosteen pericarp ethyl acetate concentrate and it would be separated into a first upper layer aqueous solution and a first lower layer precipitate after homogenizing and being placed at room temperature for a while; then, to isolate the first upper layer aqueous solution and to add amount of ethanol with ratio of weight to volume of 1:1 to dissolve the first lower layer precipitate, and be filtered to obtain a mangosteen pericarp ethanol filtrate; and then α-Xones Aqua Choice can be obtained by spray drying the mangosteen pericarp aqueous solution concentrate and the first upper layer aqueous solution, wherein the α-Xones Aqua Choice containing about 1% of mangosteen water-soluble polyphenol and the percent yield is 20% to the initial weight of mangosteen pericarp. Moreover, N-hexane is added with volume ratio is 1:5 into the mangosteen pericarp ethanol filtrate and it would be separated into an upper layer alkane solvent and a lower layer ethanol filtrate after is mixed by vortex mixer to suspension state and being placed at room temperature for a while; the lower layer ethanol filtrate is heated in water bath at 45 to 50° C. and the is concentrated to obtaining a lower layer ethanol concentrated filtrate and then distilled water is added with volume ratio is 1:1.5 and it would be separated into a second upper layer aqueous solution and a second lower layer precipitate after mixing and being placed at 6° C. overnight; Final, to perform fragmenting, spray drying at 40° C., and grinding to obtain α-Xones Prime, wherein the α-Xones Prime containing at least 50% of xanthone (based on the total content of α-mangostin and γ-mangostin) and the percent yield is 10% to the initial weight of mangosteen pericarp.

Example 2

To obtain fragment of mangosteen pericarp by drying and fragmenting the mangosteen pericarp and then the fragment is divided and packaged to a food grade of stainless-steel filter bucket. The fragment of mangosteen pericarp is soaked in ethanol with the ratio of weight to volume of 1:20 and the concentration of 90% and is placed at room temperature overnight and then to perform filtering to obtain a mangosteen pericarp ethanol extract. Next, the fragment of mangosteen pericarp is soaked in distilled water with ratio of weight to volume of 1:10 and is placed at room temperature overnight after heating at 95° C. for two hours; mangosteen pericarp water extract and mangosteen pericarp residue both be isolated by filter, and then α-Xones Prebio can be generated by spray drying and grinding the mangosteen pericarp residue at 40 to 60° C. Next, to concentrate the mangosteen pericarp ethanol extract and the mangosteen pericarp water extract to obtain a mangosteen pericarp ethanol concentrate and a mangosteen pericarp water concentrate, and then spray drying the mangosteen pericarp ethanol concentrate to obtain α-Xones Extract, wherein the α-Xones Extract containing about 30% of xanthone (based on the total content of α-mangostin and γ-mangostin) and the percent yield is 60% to the initial weight of mangosteen pericarp. Moreover, to add amount of distilled water into the mangosteen pericarp ethanol concentrate and it would be separated into a first upper layer aqueous solution and a first lower layer precipitate after homogenizing and being placed at room temperature for a while; then, to isolate the first upper layer aqueous solution and to add amount of ethanol with ratio of weight to volume of 1:1 to dissolve the first lower layer precipitate, and be filtered to obtain a mangosteen pericarp ethanol filtrate; and then α-Xones Aqua Choice can be obtained by spray drying the mangosteen pericarp aqueous solution concentrate and the first upper layer aqueous solution, wherein the α-Xones Aqua Choice containing about 5% of mangosteen water-soluble polyphenol and the percent yield is 20% to the initial weight of mangosteen pericarp. Moreover, N-hexane is added with volume ratio is 1:5 into the mangosteen pericarp ethanol filtrate and it would be separated into an upper layer alkane solvent and a lower layer ethanol filtrate after is mixed by vortex mixer to suspension state and being placed at room temperature for a while; the lower layer ethanol filtrate is heated in water bath at 45 to 50° C. and the is concentrated to obtaining a lower layer ethanol concentrated filtrate and then distilled water is added with volume ratio is 1:1 and it would be separated into a second upper layer aqueous solution and a second lower layer precipitate after mixing and being placed at 6° C. overnight; Final, to perform fragmenting, spray drying at 40° C., and grinding to obtain α-Xones Prime, wherein the α-Xones Prime containing at least 50% of xanthone (based on the total content of α-mangostin and γ-mangostin) and the percent yield is 10% to the initial weight of mangosteen pericarp.

Example 3

To obtain fragment of mangosteen pericarp by drying and fragmenting the mangosteen pericarp and then the fragment is divided and packaged to a food grade of stainless-steel filter bucket. The fragment of mangosteen pericarp is soaked in chloroform with the ratio of weight to volume of 1:5 and the concentration of 70% and is placed at room temperature overnight and then to perform filtering to obtain a mangosteen pericarp chloroform extract. Next, the fragment of mangosteen pericarp is soaked in distilled water with ratio of weight to volume of 1:20 and is placed at room temperature overnight after heating at 95° C. for two hours; mangosteen pericarp water extract and mangosteen pericarp residue both be isolated by filter, and then α-Xones Prebio can be generated by spray drying and grinding the mangosteen pericarp residue at 40 to 60° C. Next, to concentrate the mangosteen pericarp chloroform extract and the mangosteen pericarp water extract to obtain a mangosteen pericarp chloroform concentrate and a mangosteen pericarp water concentrate, and then spray drying the mangosteen pericarp chloroform concentrate to obtain α-Xones Extract, wherein the α-Xones Extract containing about 10% of xanthone (based on the total content of α-mangostin and γ-mangostin) and the percent yield is 80% to the initial weight of mangosteen pericarp. Moreover, to add amount of formic acid into the mangosteen pericarp chloroform concentrate and it would be separated into a first upper layer aqueous solution and a first lower layer precipitate after homogenizing and being placed at room temperature for a while; then, to isolate the first upper layer aqueous solution and to add amount of ethanol with ratio of weight to volume of 1:1.2 to dissolve the first lower layer precipitate, and be filtered to obtain a mangosteen pericarp chloroform filtrate; and then α-Xones Aqua Choice can be obtained by spray drying the mangosteen pericarp aqueous solution concentrate and the first upper layer aqueous solution, wherein the α-Xones Aqua Choice containing about 3% of mangosteen water-soluble polyphenol and the percent yield is 15% to the initial weight of mangosteen pericarp. Moreover, N-hexane is added with volume ratio is 1:10 into the mangosteen pericarp chloroform filtrate and it would be separated into an upper layer alkane solvent and a lower layer chloroform filtrate after is mixed by vortex mixer to suspension state and being placed at room temperature for a while; the lower layer chloroform filtrate is heated in water bath at 45 to 50° C. and the is concentrated to obtaining a lower layer chloroform concentrated filtrate and then distilled water is added with volume ratio is 2:1 and it would be separated into a second upper layer aqueous solution and a second lower layer precipitate after mixing and being placed at 6° C. overnight; Final, to perform fragmenting, spray drying at 40° C., and grinding to obtain α-Xones Prime, wherein the α-Xones Prime containing at least 50% of xanthone (based on the total content of α-mangostin and γ-mangostin) and the percent yield is 10% to the initial weight of mangosteen pericarp.

Component Analysis of the Extract

Figure 1B:
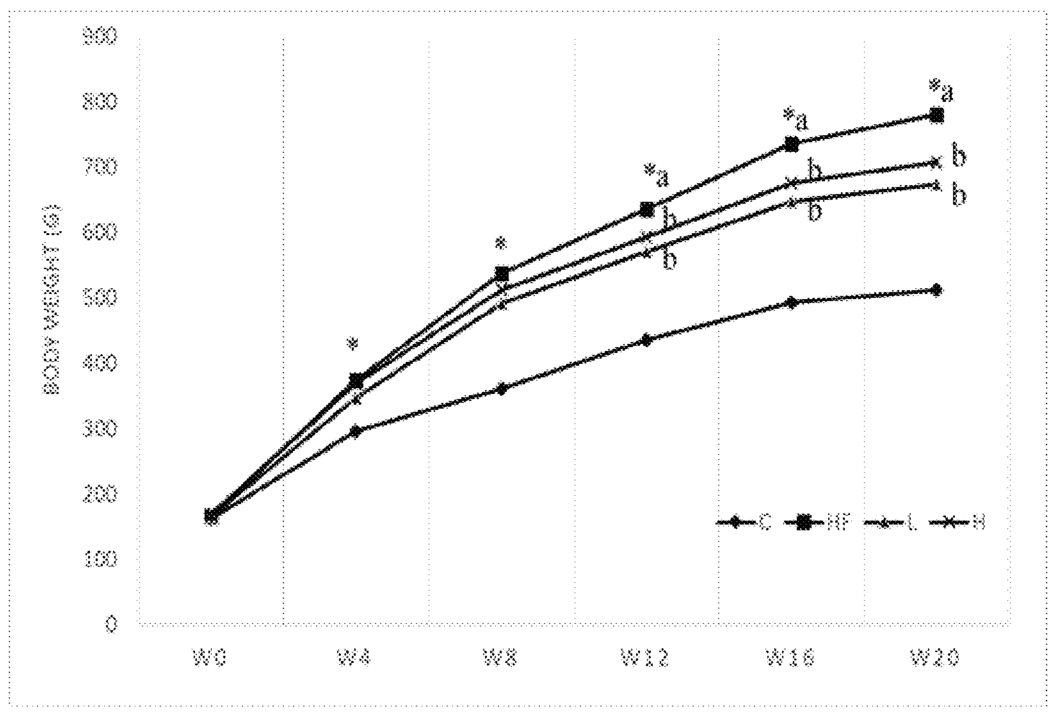
FIG. 1(B) shows body weight during 20 weeks of treatment. Values are presented as the mean±SEM (n=8). *Significantly different between C and HF groups. $^{abc}$Value in columns with different letters mean significant difference ($p<0.05$). C, control diet; HF, high fat diet; L, high fat diet with low dose α-Xones Prime; H, high fat diet with high dose α-Xones Prime.

Please refer to FIG. 1(*a*) which shows an analysis result of ratio of α-mangostin and γ-mangostin in the extract of the present invention. The analysis is conducted by high performance liquid chromatography (HPLC) analysis for the α-Xones Extract (low purity of the mangosteen pericarp extract containing 10% to 30% of xanthone) and α-Xones Prime (high purity of the mangosteen pericarp extract containing 50% of xanthone) which obtained from example 2. The experiment detail is shown, SUPELCO INC. reverse phase, Waters Spherisorb ODS-2, 5 μm. 250 mm×4.6 mm or similar columns; flow rate of mobile phase: 1 mL/min; mobile phase containing solution A which is 0.1% formic acid solution and solution B which is acetonitrile; wavelength is 250 to 260 nm; and the mobile phase gradient is adjusted as follows:

| | Solution A | Solution B |
|---|---|---|
| Starting | 35% | 65% |
| 25 minutes | 0% | 100% |
| 28 minutes | 35% | 65% |
| 30 minutes | 35% | 65% |

As shown in FIG. 1(*a*), two significant peaks representing α-mangostin and γ-mangostin. By comparing their absorbance signal or/and area for those two peaks, we can know that the percentage of α-mangostin and γ-mangostin is 65~75% and 10~15%. Therefore, the process for preparing mangosteen pericarp extract from present invention could obtain different kind with different content of mangosteen pericarp extract which including 65~75% of α-mangostin and 10~15% of γ-mangostin. Moreover, it could be represented by the ratio of α-mangostin and γ-mangostin which is 5~7.

In view of the above, after implementation of the present invention, the objective of providing a simple preparation steps to address efficiency issue and with advantage of having α-mangostin and γ-mangostin in the extract product from the rind of the mangosteen in the same preparation process can be successfully achieved. Moreover, the present invention has advantage of no need to have heating under reflux in extraction steps and the solvents which used are more safe and eco-friendly.

The description of comprise, have, include, contain, or another similar semantics has the non-exclusive meaning. For example, an element, structure, product, or device contain multi requirements are not limited in the list of the content, but include another inherent requirement of element, structure, product or device not explicitly listed in the content. In addition, the term "or" is inclusive meaning, and not exclusive meaning.

The present invention is disclosed by the preferred embodiment in the aforementioned description; however, it is contemplated for one skilled at the art that the embodiments are applied only for an illustration of the present invention rather than are interpreted as a limitation for the scope of the present invention. It should be noted that the various substantial alternation or replacement equivalent to these embodiments shall be considered as being covered within the scope of the present invention. Therefore, the protection scope of the present invention shall be defined by the claims.

Materials and Methods

Mangosteen Pericarp Ethanolic Extract (α-Xones Prime) Preparation

The mangosteen pericarp extract preparation process of the present invention is first drying and fragmenting the mangosteen pericarp to obtain fragment of mangosteen pericarp. To facilitate subsequent extraction operations, the fragment could be divided and packaged by food grade of cotton filter bags or stainless-steel filter buckets. The fragment of mangosteen pericarp is soaked in organic solvent with certain concentration and ratio and is placed at room temperature for a while, and then to perform filtering to obtain a mangosteen pericarp organic solvent extract, wherein the certain ratio means the weight to volume of the fragment of mangosteen pericarp and the organic solvent is 1:5 to 1:20, preferably 1:5 to 1:10, and the certain concentration means volume percentage concentration is at least 70%, preferably at least 80%, more preferably at least 90%, the organic solvent including but not limit to methanol, ethanol, acetic acid, ethyl acetate and chloroform. Following soaked in organic solvent, the fragment of mangosteen pericarp is soaked in aqueous solution with certain ratio and is placed at room temperature after heating, and then is filtered to obtain a mangosteen pericarp aqueous extract and a mangosteen pericarp residue, wherein the ratio means the weight to volume of the fragment of mangosteen pericarp and the aqueous solution is 1:10 to 1:20, preferably 1:10 to 1:20. To concentrate the mangosteen pericarp organic solvent extract and the mangosteen pericarp aqueous extract to obtain a mangosteen pericarp organic solvent concentrate and a mangosteen pericarp aqueous concentrate. Following the process mentioned above, the process further comprising the steps of adding amount of the aqueous or acidic solution into the mangosteen pericarp organic solvent concentrate and homogenizing, and be separated into a first upper layer aqueous solution and a first lower layer precipitate after being placed at room temperature for a while, then isolating the first upper layer aqueous solution and adding amount of ethanol to dissolve the first lower layer precipitate and be filtered to obtain a mangosteen pericarp ethanol filtrate; Following the process mentioned above, the process further comprising the steps of adding alkane solvent with volume ratio is 1:1 to 1:10 into the mangosteen pericarp ethanol filtrate and mixing it to as suspension by vortex mixer and be separated into an upper layer alkane solvent and a lower layer ethanol filtrate after being placed at room temperature for a while, wherein the alkane solvent refers to alkanes in liquid form at room temperature, which including but not limit to N-pentane, N-hexane, and N-heptane. Next, the lower layer ethanol filtrate is isolated and heated in water bath and is concentrated at low temperature to obtain a lower layer ethanol concentrated filtrate and then to add and mix aqueous solution with volume ratio is 1:1 to 3:1 into the lower layer ethanol concentrated filtrate, and it would be separated into a second upper layer aqueous solution and a second lower layer precipitate after being placed at low temperature for a while. Then, α-Xones Prime can be obtained by fragmenting, spray drying, and grinding the second lower layer precipitate, especially, the α-Xones Prime in the present invention refers to a high purity of the mangosteen pericarp extract containing at least 50% of xanthone.

To achieve the objectives, a preparation process for mangosteen pericarp extract of the present invention comprising:

drying and fragmenting the mangosteen pericarp to obtain fragment of mangosteen pericarp;

soaking the fragment of mangosteen pericarp in organic solvent with a concentration of at least 70% and placing it at room temperature, and filtering it to obtain a mangosteen pericarp organic solvent extract, wherein the ratio of the weight to volume of the fragment of mangosteen pericarp and the organic solvent is 1:5 to 1:20;

soaking and heating the fragment of mangosteen pericarp obtained from the previous step in aqueous solution and placing it at room temperature, and filtering it to obtain a mangosteen pericarp aqueous extract and a mangosteen pericarp residue, wherein the ratio of the weight to volume of the fragment of mangosteen pericarp and the aqueous solution is 1:10 to 1:20;

concentrating the mangosteen pericarp organic solvent extract and the mangosteen pericarp aqueous extract to obtain a mangosteen pericarp organic solvent concentrate and a mangosteen pericarp aqueous concentrate; and adding a first specific amount of the aqueous or acidic solution into the mangosteen pericarp organic solvent concentrate, homogenizing it, placing it at room temperature, and separating it into a first upper layer aqueous solution and a first lower layer precipitate;

isolating the first upper layer aqueous solution and adding a second specific amount of ethanol to dissolve the first lower layer precipitate, and obtaining a mangosteen pericarp ethanol filtrate by filtration; and The process mentioned above further comprising the following steps:

adding alkane solvent with volume ratio is 1:1 to 1:10 into the mangosteen pericarp ethanol filtrate and mixing by vortex mixer, placing it at room temperature, and separating it into an upper layer alkane solvent and a lower layer ethanol filtrate;

heating and concentrating the lower layer ethanol filtrate in water bath to obtaining a lower layer ethanol concentrated filtrate, and adding and mixing aqueous solution with volume ratio is 1:1 to 3:1 into the lower layer ethanol concentrated filtrate, placing it at low temperature, and separating it into a second upper layer aqueous solution and a second lower layer precipitate; and fragmenting, air-lay drying and grinding the second lower layer precipitate to obtain α-Xones Prime, wherein the α-Xones Prime containing at least 50% of xanthones. The composition obtained by the isolation method of the present invention contains α-mangosteen and γ-mangosteen at a certain ratio (65% of α-mangostin and 10% of γ-mangostin). Furthermore, it can be ingested as a health food in the form of various foods and beverages.

Animals and Experimental Procedures

Thirty-two male Sprague Dawley rats, 6 weeks old, were purchased from BioLASCO Taiwan Co., Ltd. (Taipei, Taiwan). Animals were housed in the air-condition room maintained at 23±2° C. with a relative humidity of 50-60% and an alternating 12 hours light/dark cycle. After one week of adaptation period, all rats were randomly divided into four groups, including control group (C), high fat diet (HF) group, low dose α-Xones Prime group (L) and high dose α-Xones Prime group (H). Each group contained 8 rats. The control group (C) fed a standard chow diet (LabDiet 5001, Land O'Lakes Inc., USA) which has compositions as shown in Table 1. The other groups fed a high fat diet prepared as shown in Table 2.

TABLE 1

| Components of Control diet | | |
|---|---|---|
| LabDiet 5001<br>Physiological Fuel Energy: 3.35 kcal/g<br>Selected Nutrition Information | | |
| | w/w % | % of total energy |
| Carbohydrate | 47.5 | 57 |
| Fat | 5 | 13 |
| Protein | 25 | 30 |

TABLE 2

| Components of HF diet | | |
|---|---|---|
| High Fat diet<br>Physiological Fuel Energy: 4.662 kcal/g | | |
| Components | | |
| LabDiet 5001 (g/kg) | 460 | |
| Soybean oil (g/kg) | 125 | |
| Lard (g/kg) | 125 | |
| Sucrose (g/kg) | 250 | |
| Casein (g/kg) | 40 | |
| Selected Nutrition Information | | |
| | w/w % | % of total energy |
| Carbohydrate | 46.9 | 37.9 |
| Fat | 27.3 | 49.6 |
| Protein | 15.5 | 12.5 |

Rats in each group were respectively provided with experimental diets and water ad libitum as well as recorded daily feed intake and body weight per week. The L and H groups were additional supplemented with 25 and 50 mg α-Xones Prime/kg BW separately by p.o. between 3 and 5 μm. After 20 weeks of treatment, fasting blood samples of all the groups were drawn by exsanguination from the abdominal aorta after anesthetization and the heart, liver, kidney, epididymal fat, inguinal fat and gastrocnemius muscle were collected. Blood samples were centrifuged with 2000×g for 10 min at 4° C. to obtain serum and all the collected samples were frozen at −80° C. until analysis. All animal experimental procedures complied with published guidelines (Kilkenny et al. 2010; Schulz et al. 2010) and were approved by the Institutional Animal Care and Use Committee of Taipei Medical University (Taipei, Taiwan; IACUC approval No: LAC-2018-0170).

Serum Biochemistry Assays

Total cholesterol (TC), high density lipoprotein-cholesterol (HDL-c), low density lipoprotein-cholesterol (LDL-c), triglycerides (TG), nonesterified fatty acids (NEFA), and glucose AC were measured using an automatic analyzer (Roche cobas c702, Roche, USA). Insulin was tested by commercially commercial reagent (Mercodia 10-1250-10, Sylveniusgatan 8A, Sweden). HOMA-IR index=insulin (μU/mL)×glucose (mmol/L)/22.5.

Histology

The gastrocnemius muscle, inguinal adipose tissue and adipose tissue were harvested after rats sacrificed and immediately rinsed with ice phosphate buffered saline (PBS) solution and immersed in 10% neutral formalin solution, fixed overnight at room temperature and then were dehydrated in 95% ethanol and then cleared in xylene before embedding in paraffin. Thick sections (8 μm) were stained with hematoxylin & cosin (H&E) and muscle sample were stained with Oil Red O staining and mounted on glass slides. Oil Red O is an oil-soluble dye used for staining neutral triglycerides and lipids. Samples were subsequently visualized under a Leica DM750 microscope with ICC50 HD camera (Leica Microsystems, Germany) and representative images were captured.

Evaluation of TG Levels in Skeletal Muscle

The skeletal muscle fat isolation was conformed as follows: 0.5 g of muscle homogenized with 3 mL of extract solvent (chloroform/methanol=2/1 (v/v)), using a polytron homogenizer. After homogenization, the mixed solution was filtered into 15 mL plastic centrifuge tube with filter paper, quantify to 4 mL with extract solvent, and then added 0.8 mL of 0.05% $CaCl_2$), and vortex mixed. After centrifugation with 3000×g for 5 minutes at 4° C., the supernatant was removed and quantified to 4.8 mL with a solvent (chloroform/methanol/water=3/48/47 (v/v/v)) and vortex mixed. After centrifuged at 4° C. with 3000×g for 5 minutes, remove the supernatant, quantify to 3.6 mL with methanol, and finally quantify to 4 mL with extract solvent, take 100 μL into a microcentrifuge tube, drain the organic solvent with a vacuum aspirator, and then dissolved in 1 mL NP-40 solution (1%, w/v). The triglycerides (TG) were measured using a commercial reagent kits (Randox TR213, Antrim, UK).

Results

Effects of α-Xones Prime on Body Weight, Food Intake and Calorie Intake

Figure 2:
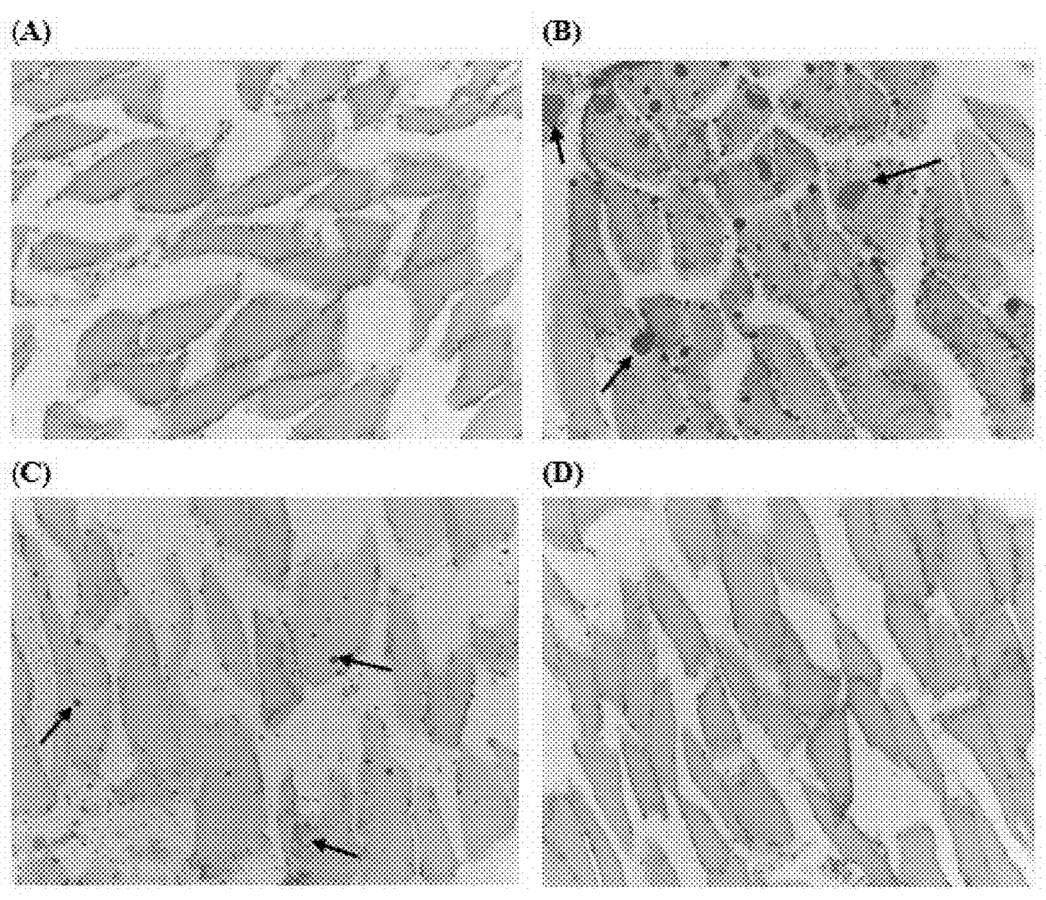
FIG. 2 shows images of Oil red O staining of muscle after 20 weeks of treatment. (100×) (A) C group. (B) HF group. (C) L group. (D) H group; C, control diet; HF, high fat diet; L, high fat diet with low dose α-Xones Prime; H, high fat diet with high dose α-Xones Prime. Photographs of oil droplets were indicated by arrows.
Figure 3:
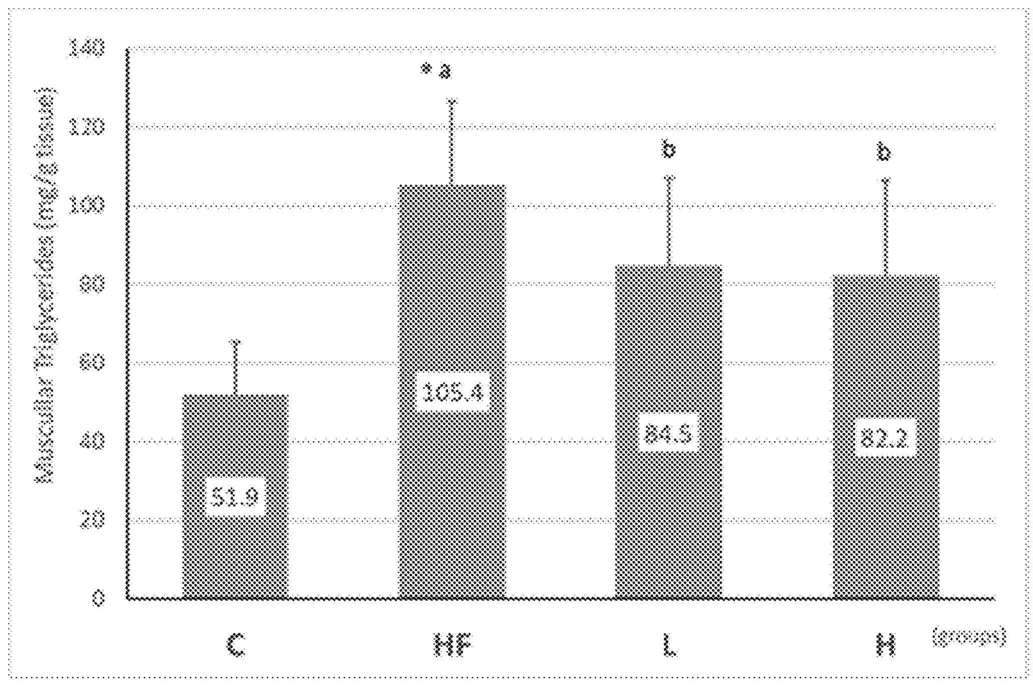
FIG. 3 shows the muscular triglyceride levels in muscle after 20 weeks with different experimental diet. Values are presented as the mean±SD (n=8). *Significantly different between C and HF groups ($p<0.05$); Value in a column with different letters of superscript mean significant different at ($p<0.05$) compared with HF group. C, control diet; HF, high fat diet; L, high fat diet with low dose α-Xones Prime; H, high fat diet with high dose α-Xones Prime.

As shown in Table 3, there was no significant difference in initial body weight between the four groups. After 20-weeks of treatment, final body weight of the HF group was significantly increased 52.4% compared with the C group, but the L and H groups were significantly lower than the HF group (11.8% and 9.4%, respectively). Furthermore, body weight gain of the HF group was significantly increased 76.3% compared with the C group, but the L and H groups were significantly lower than the HF group (17.6% and 18.1%, respectively) during 20 weeks period (Table 3). Body weight of the high fat diet groups increased significantly compared with the C group from the $4^{th}$ week to the $20^{th}$ week. However, body weight of the L and H groups were significantly lower than the HF group from the $8^{th}$ week to the $20^{th}$ week, but there was no significant difference between the two groups during the period (FIG. 2).

TABLE 3

Body weight and Food intake[1, 2]

| | C | HF | L | H |
|---|---|---|---|---|
| Initial weight (g) | 163.1 ± 7.8 | 165.3 ± 5.4[a] | 166.0 ± 7.6[a] | 169.3 ± 6.8[a] |
| Final weight (g) | 512.1 ± 23.4 | 780.4 ± 58.1*[a] | 673.0 ± 45.1[b] | 707.0 ± 32.4[b] |
| Weight gains (g) | 349.0 ± 20.1 | 615.1 ± 56.9*[a] | 507.0 ± 44.8[b] | 503.7 ± 45.9[b] |
| Food intake (g/day) | 16.63 ± 0.08 | 15.59 ± 0.54*[b] | 16.20 ± 0.23[a] | 15.83 ± 0.74[ab] |
| Food intake (kcal/day) | 55.70 ± 0.25 | 72.67 ± 2.55*[b] | 75.43 ± 1.07[a] | 73.65 ± 3.37[ab] |

[1]Values are presented as the mean ± SD, n = 8; C, control diet; HF, high fat diet; L, high fat diet with low dose α-Xones Prime; H, high fat diet with high dose α-Xones Prime; Feed efficiency = weight gains/food intake.
[2]"*" Significantly different between C and HF groups at $p < 0.05$; Value with different letters of superscript mean significant different compared with HF group at $p < 0.05$.

Food intake in the HF group during the 20 weeks was significantly lower than in the C group. there was a significant increase in the L group compared with the HF group. There was no significant difference between the H group and the HF group. And the caloric intake of the high fat diet groups was all significantly increased compared with the C group, while the L group was significantly increased compared with the HF group, but no difference between the H group and the L group. These results reveal mangosteen pericarp ethanolic extract administration can decrease weight gain during daily high diet intake.

Effects of α-Xones Prime on Organ Weight and Adipose Tissue Weight in Rats

As shown in Table 4, The weight of the heart, liver, kidney and muscle were significantly increased in the HF group compared with the C group (28.4%, 16.9%, 8.3% and 23.9%, respectively). However, heart weight of the L and H groups were significantly lower than the HF group (10.6% and 8.7%, respectively), while kidney weight of the L and H groups were significantly lower than the HF group (9.85% and 9.85%, respectively). Although, there was no significant difference, liver weight of the L and H groups were lower than the HF group (5.77% and 3.57%, respectively) but muscle weight of the L and H groups were increased 5.41% and 7.12% compared to the HF group, respectively.

TABLE 4

Organ weight and adipose tissue weight[1, 2]

| | C | HF | L | H |
|---|---|---|---|---|
| Heart (g) | 1.62 ± 0.20 | 2.08 ± 0.14*[a] | 1.86 ± 0.17[b] | 1.90 ± 0.14[b] |
| Liver (g) | 17.49 ± 1.61 | 20.44 ± 2.18*[a] | 19.26 ± 1.07[a] | 19.71 ± 1.90[a] |
| Kidney (g) | 3.75 ± 0.25 | 4.06 ± 0.25*[a] | 3.66 ± 0.25[b] | 3.66 ± 0.23[b] |
| Muscle (g) | 11.34 ± 1.19 | 14.05 ± 0.87*[a] | 14.81 ± 0.96[a] | 15.05 ± 0.63[a] |
| Epididymal fat (g) | 7.29 ± 1.27 | 22.75 ± 5.29*[a] | 17.34 ± 3.03[b] | 18.84 ± 2.40[b] |
| Epididymal fat/BW (%) | 1.42 ± 0.23 | 2.93 ± 0.46*[a] | 2.52 ± 0.31[b] | 2.61 = 0.25[b] |
| Inguinal fat (g) | 7.56 ± 1.84 | 32.75 ± 7.69*[a] | 18.17 ± 6.62[b] | 23.01 ± 6.79[b] |
| Inguinal fat/BW (%) | 1.47 ± 0.31 | 4.38 ± 0.68*[a] | 2.64 ± 0.76[b] | 3.15 ± 0.85[b] |

[1]Values are presented as the mean ± SD, n = 8; C, control diet; HF, high fat diet; L, high fat diet with low dose α-Xones Prime; H, high fat diet with high dose α-Xones Prime.
[2]"*" Significantly different between C and HF groups at $p < 0.05$; Value with different letters of superscript mean significant different compared with HF group at $p < 0.05$.

The weight of the epididymal fat and the inguinal fat were significantly increased in the HF group compared with the C group (212.1% and 333.2%, respectively). However, epididymal fat weight of the L and H groups were significantly lower than the HF group (23.8% and 20.1%, respectively), while inguinal fat weight of the L and H groups were significantly lower than the HF group (44.5% and 29.7%, respectively). The proportion of epididymal fat weight/body weight was significantly higher in the HF group than in the C group, but the L group and H group was significantly lower than the HF group. The proportion of inguinal fat weight/body weight was significantly higher in the HF group than in the C group, but the L group and H group was significantly lower than the HF group (Table 4). These results reveal mangosteen pericarp ethanolic extract administration can decrease fat accumulation during daily high fat diet intake.

Effects of α-Xones Prime on Fasting Plasma Glucose, Insulin, and Lipids

As shown in Table 5, fasting blood glucose was significantly increased in the HF group compared with the C group, but the L and The H group were significantly lower than the HF group (11.3% and 15.6%, respectively). The insulin concentration and the insulin resistance index HOMA-IR were significantly increased in the HF group compared with the C group (86.7% and 195.1%, respectively). Although, there was no significant difference, insulin concentrations of the L and H groups were lower than the HF group (19.7% and 23.5%, respectively), and HOMA-IR of the L and H groups were decreased 19.5% and 30.7% compared to the HF group, respectively. Although, there was no significant difference in triglycerides and cholesterol levels between four groups, but the high fat diet groups were higher than the C group (Table 5). Furthermore, the NEFA concentrations of the high fat diet groups (HF, L and H) were significantly all increased compared with the C group but no significant difference between these groups.

TABLE 5

Blood glucose and lipid profiles of the experimental groups after 20 weeks of treatment[1, 2]

| | C | HF | L | H |
|---|---|---|---|---|
| Glucose (mg/dL) | 147.3 ± 11.4 | 240.4 ± 16.4*[a] | 213.3 ± 14.5[b] | 203.0 ± 12.1[b] |
| Insulin (μg/L) | 2.78 ± 1.10 | 5.19 ± 1.98*[a] | 4.22 ± 1.39[a] | 3.97 ± 1.56[a] |
| HOMA-IR | 23.99 ± 9.03 | 70.80 ± 29.64*[a] | 57.03 ± 20.96[a] | 49.08 ± 20.65[a] |
| TG (mg/dL) | 95.1 ± 26.6 | 139.0 ± 71.1 | 103.0 ±19.9 | 101.1 ± 39.6 |

TABLE 5-continued

Blood glucose and lipid profiles of the experimental groups after 20 weeks of treatment[1, 2]

| | C | HF | L | H |
|---|---|---|---|---|
| TC (mg/dL) | 57.25 ± 4.30 | 69.63 ± 14.74 | 53.50 ± 9.11 | 62.63 ± 15.13 |
| NEFA (mM) | 0.60 ± 0.20 | 1.24 ± 0.33*[a] | 1.16 ± 0.18[a] | 1.38 ± 0.32[a] |

[1]Values are presented as the mean ± SD, n = 8; C, control diet; HF, high fat diet; L, high fat diet with low dose α-Xones Prime; H, high fat diet with high dose α-Xones Prime.
[2]"*" Significantly different between C and HF groups at $p < 0.05$; Value with different letters of superscript mean significant different compared with HF group at $p < 0.05$.

Effect of α-Xones Prime on Muscle Tissue

As shown in FIG. 2, the Oil red O staining images shows the lipid droplets of the HF group were found to be most than the other groups, that reveals more oil droplets than the C group. In the high fat diet groups, the oil droplets were less and smaller in the L and H groups compared with the HF group. In addition, the muscular triglycerides content of the HF group was significantly increased 103.1% compared with the C group. However, the muscular triglycerides content of the L and H groups were significantly lower than the HF group (19.8% and 22.0%, respectively). These results demonstrated mangosteen pericarp ethanolic extract administration can decrease fat accumulation in the muscle tissue caused by daily high fat diet intake.

Effect of α-Xones Prime on Adipose Tissue

Figure 4:
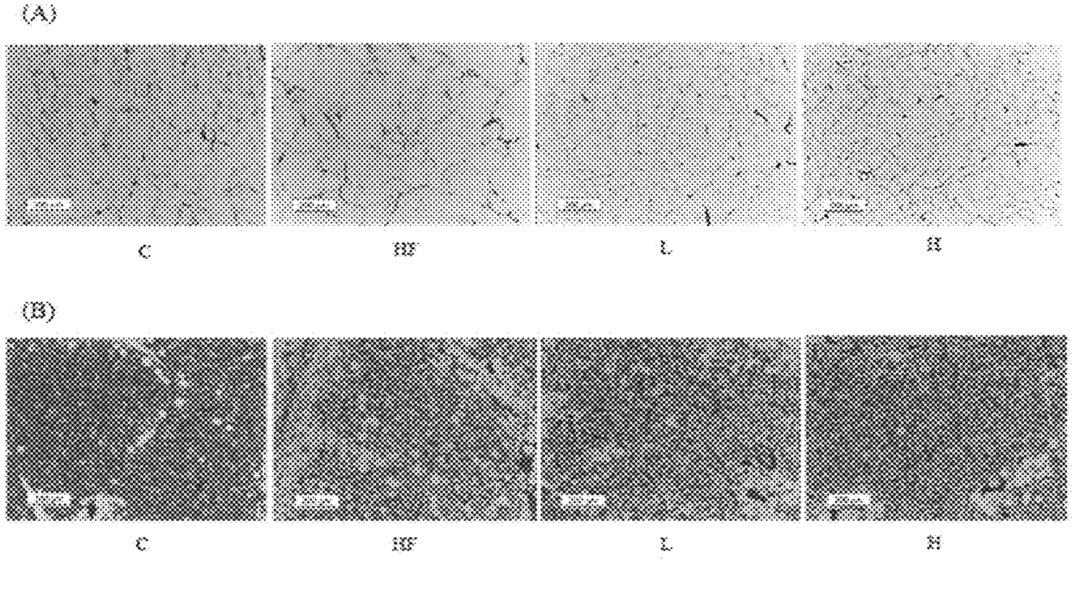
FIG. 4 is a panel that shows epididymal adipose tissue (A) and interscapular adipose tissue (B) sections by using H&E stained (40×). C, control diet; HF, high fat diet; L, high fat diet with low dose α-Xones Prime; H, high fat diet with high dose α-Xones Prime.

Histologically, white fat cells are characterized by a single large lipid droplet, flattened and eccentric nuclei, and scanty cytoplasm surrounding the lipid droplet. As shown in FIG. 4 (A) & (B), the lipid droplets of the HF group were found to be largest than the other groups, that present the oil droplets were larger than the C group, while the Land H groups were found to have smaller oil droplets compared with the HF group (FIG. 4). These results reveal mangosteen pericarp ethanolic extract administration can decrease fat accumulation in the adipose tissues caused by daily high fat diet intake.

What is claimed is:

1. A method for inhibiting weight gain, insulin resistance, and fat accumulation in adipose and muscle tissue induced by a high fat diet in a human in need thereof consisting essentially of administering to the human in need thereof a therapeutically effective amount of an extract of mangosteen pericarp, wherein the extract of the mangosteen pericarp extract is made by a process consisting essentially of: a) drying and fragmenting a mangosteen pericarp to obtain a fragment of the mangosteen pericarp; b) soaking the fragment of the mangosteen pericarp in at least 70% ethanol to yield a mangosteen pericarp extract and holding it at room temperature; c) filtering the mangosteen pericarp extract to obtain a mangosteen pericarp organic solvent extract, wherein the ratio of the weight to volume of the fragment of mangosteen pericarp and the organic solvent is 1:2 to 1:20; d) soaking and heating the fragment of mangosteen pericarp organic solvent extract of step c) in an aqueous solution and holding it at room temperature; e) filtering it to obtain a mangosteen pericarp aqueous extract and a mangosteen pericarp residue, wherein the ratio of the weight to volume of the fragment of mangosteen pericarp and the aqueous solution is 1:10 to 1:20; f) concentrating the mangosteen pericarp organic solvent extract and the mangosteen pericarp aqueous extract to obtain a mangosteen pericarp organic solvent concentrate and a mangosteen pericarp aqueous concentrate; g) adding the mangosteen pericarp organic solvent concentrate to an aqueous solution; h) homogenizing it, holding it at room temperature; i) separating it into a first upper layer aqueous solution and a first lower layer precipitate; j) isolating the first upper layer aqueous solution and adding ethanol to dissolve the first lower layer precipitate; k) obtaining a mangosteen pericarp ethanol extract by filtration; l) adding alkane solvent with a volume ratio of 1:1 to 1:10 into the mangosteen pericarp ethanol extract and mixing it with a vortex mixer, holding it at room temperature; m) separating it into an upper layer alkane solvent and a lower layer ethanol filtrate; n) heating and concentrating the lower layer ethanol filtrate in water bath to obtain a lower layer ethanol concentrated filtrate; o) adding and mixing aqueous solution with a volume ratio of 1:1 to 3:1 into the lower layer ethanol concentrated filtrate, holding it at low temperature; p) separating it into a second upper layer aqueous solution and a second lower layer precipitate; and q) fragmenting, air-lay drying and grinding the second lower layer precipitate to obtain the mangosteen pericarp ethanol extract.

* * * * *